United States Patent
Dannheim et al.

(10) Patent No.: US 10,758,159 B2
(45) Date of Patent: Sep. 1, 2020

(54) MEASURING SOMATIC RESPONSE TO STIMULUS UTILIZING A MOBILE COMPUTING DEVICE

(71) Applicant: Sensie, LLC, Miami, FL (US)

(72) Inventors: Mike Dannheim, Miami, FL (US); Thomas Gersten, San Diego, CA (US); Edgar Alberto Herrador Nieto, Mexico City (MX)

(73) Assignee: SENSIE, LLC, Miami, FL (US)

( * ) Notice: Subject to any disclaimer, the term of this patent is extended or adjusted under 35 U.S.C. 154(b) by 860 days.

(21) Appl. No.: 15/397,463

(22) Filed: Jan. 3, 2017

(65) Prior Publication Data

US 2018/0189451 A1 Jul. 5, 2018

(51) Int. Cl.
*G16H 40/60* (2018.01)
*G16H 50/70* (2018.01)
(Continued)

(52) U.S. Cl.
CPC .......... *A61B 5/1104* (2013.01); *A61B 5/4029* (2013.01); *A61B 5/6898* (2013.01);
(Continued)

(58) Field of Classification Search
CPC ........ G16H 10/60; G16H 30/40; G16H 40/67; A61B 5/1171; A61B 90/37; A61B 3/0041; A61B 3/10; A61B 3/113; A61B 5/0077; A61B 5/044; A61B 5/06; A61B 5/1176; A61B 5/4803; A61B 2034/2048; A61B 2090/365; A61B 2090/372; A61B 2090/502; A61B 2017/00207; A61B 2017/00216; G02B 27/0093; G02B 27/0172; G02B 2027/0127; G02B 2027/138; G02B 2027/014;
(Continued)

(56) References Cited

U.S. PATENT DOCUMENTS

| | | | |
|---|---|---|---|
| 2015/0164377 A1* | 6/2015 | Nathan | A61B 5/1122 600/595 |
| 2015/0338917 A1* | 11/2015 | Steiner | H04L 9/3231 345/156 |
| 2018/0052913 A1* | 2/2018 | Gaskill | G06F 16/3344 |

FOREIGN PATENT DOCUMENTS

WO WO-2015192239 A1 * 12/2015 ........... G06K 9/6254

OTHER PUBLICATIONS

Weil, Dr. Andrew, Applied Kinesiology, 2016, https://web.archive.org/web/20160829184253/https://www.drweil.com/health-wellness/balanced-living/wellness-therapies/applied-kinesiology/ (Year: 2016).*
(Continued)

*Primary Examiner* — Jonathan Durant
*Assistant Examiner* — Anne-Marie K Alderson
(74) *Attorney, Agent, or Firm* — Mark Terry (57) ABSTRACT

A mobile computing device for measuring somatic response of a user to stimulus includes motion sensors, a volatile memory, and a processor for: executing a baseline calibration process including receiving first and second supervised data from the user, and first and second sensor data from the motion sensors, while the user performs a triple whip gesture, calculating signal strength of the first and second sensor data using a k-means clustering algorithm, and executing a classification process including reading third unsupervised data from the user and third sensor data from the motion sensors while the user performs the triple whip gesture.

18 Claims, 6 Drawing Sheets

(51) Int. Cl.
　　　*G16H 40/67*　　　　(2018.01)
　　　*A61B 5/11*　　　　 (2006.01)
　　　*A61B 5/00*　　　　 (2006.01)

(52) U.S. Cl.
　　　CPC ........... *A61B 5/7264* (2013.01); *G16H 40/60* (2018.01); *G16H 40/67* (2018.01); *G16H 50/70* (2018.01)

(58) Field of Classification Search
　　　CPC ............. G02B 2027/141; G10L 15/265; G06F 21/6245; G06F 16/22; G06F 16/2379; G06F 17/2705; G06F 17/2775; G06F 21/32; G06K 9/00671
　　　See application file for complete search history.

(56) References Cited

OTHER PUBLICATIONS

Gaggioli, Andrew, et. al., A System for Automatic Detection of Momentary Stress in Naturalistic Settings, Studies in health technology and informatics, 181:182-6, Sep. 2012 (Year: 2012).*

Smith, Briallyn, "How to Test your Self-Awareness & Lift Every Area of Your Life", https://www.makeuseof.com/tag/test-self-awareness-lift-every-area-life/, Jun. 13, 2016 (Year: 2016).*

\* cited by examiner

MEASURING SOMATIC RESPONSE TO STIMULUS UTILIZING A MOBILE COMPUTING DEVICE

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to the detection and identification of the human body's somatic responses to stimuli.

BACKGROUND

Measuring the human body's response to stimuli is the subject of significant research and development. Often, a patient's voluntary nervous system is evaluated in order to study the human body's response to stimuli. The voluntary nervous system, also known as the somatic nervous system, is the part of the peripheral nervous system associated with skeletal muscle voluntary control of body movements. The somatic nervous system controls all voluntary muscular systems within the body, as well as reflex arcs.

A wide array of methods are used to measure the human body's response to stimuli. Galvanic skin response sensors, for example, measure electrodermal activity, which is the property of the human body that causes continuous variation in the electrical characteristics of the skin. Skin resistance varies with the state of sweat glands in the skin. Sweating is controlled by the sympathetic nervous system, and skin conductance is an indication of psychological or physiological arousal. If the sympathetic branch of the autonomic nervous system is highly aroused, then sweat gland activity also increases, which in turn increases skin conductance. In this way, skin conductance can be a measure of emotional and sympathetic responses. In another example, bioelectrical impedance analysis can be used to determine the electrical impedance, or opposition to the flow of an electric current through body tissues. In yet other examples, blood pressure and heart rate can be measured, which indicates the level of a human body's arousal, wakefulness and/or ability to adjust to one's surroundings.

One of the drawbacks associated with a currently available methods for measuring the human body's response to stimuli is the complexity of the devices used. Galvanic skin response systems, for example, require the use of dermal sensors, wires, and a dedicated computer system to gather the information required and formulate a measurement. This can be difficult and tedious for operators of the system to utilize. Another drawback associated with currently available methods for measuring the human body's response to stimuli is the size and handling of the devices used. Galvanic skin responses systems, for example, are large systems that require shelf space, a power outlet and a working area. This can be disadvantageous for users that intend to use the system on the go, in the field, or in small or cramped quarters where there is little or no space available.

Therefore, a need exists for improvements over the prior art, and more particularly for more efficient methods and systems for detecting and identifying the human body's somatic responses to stimuli.

SUMMARY

A method and system for measuring somatic response of a user to stimulus is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a mobile computing device for measuring somatic response of a user to stimulus includes a plurality of motion sensors configured for capturing motion sensor data, a volatile memory, and a processor communicatively coupled with the plurality of motion sensors and the memory, the processor configured for: executing a baseline calibration process comprising: i) receiving a first supervised data comprising a negative type and a first sensor data from the plurality of motion sensors while the user performs a triple whip gesture comprising a wrist movement executed three times while holding the mobile computing device; ii) classifying the first sensor data according to a predefined criteria and associating class data with the first sensor data; iii) receiving a second supervised data comprising a positive type and a second sensor data from the plurality of motion sensors while the user performs the triple whip gesture; iv) classifying the second sensor data according to the predefined criteria and associating class data with the second sensor data, and calculating signal strength of the first and second sensor data using a k-means clustering algorithm, wherein the first and second sensor data are clustered based on one or more features of the triple whip gesture embodied in the first and second sensor data, and wherein signal strength comprises a confidence level that unsupervised data may be classified based on the first and second sensor data and class data associated therewith, and executing a classification process comprising: i) reading third unsupervised data comprising third sensor data from the plurality of motion sensors while the user performs the triple whip gesture, ii) classifying the third sensor data in a cluster defined by the k-means clustering algorithm and associating class data with the third sensor data; and iii) determining a type of the third sensor data, based on the class data.

BRIEF DESCRIPTION OF THE DRAWINGS

The accompanying drawings, which are incorporated in and constitute a part of this disclosure, illustrate various example embodiments. In the drawings.

DETAILED DESCRIPTION

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims.

The claimed subject matter improves over the prior art by providing a more efficient, automated and precise way of measuring somatic response of a user to stimulus. The example embodiments utilize and leverage widely available smart phones or other mobile computing devices to measure somatic response of a user to stimulus. The example embodiments provide a simple and user-friendly method and device which is easy for operators of the system to utilize. The example embodiments also provide a small, handheld system that requires little to no shelf space, and does not require a power outlet or a working area. This is advantageous for users that use the system on the go, in the field or in small or cramped quarters where there is little or no space available. Lastly, the claimed subject matter can be used to determine a user's alignment with his or her conscious self and/or subconscious self. This provides an easy to understand indicator to the user of his or her psychological state.

A user's somatic response to stimuli is indicative of various aspects of a person's physical and psychological state. Thus, a user's somatic response to stimuli may be an indication of psychological or physiological arousal, his emotional state, his wakefulness and/or his ability to adjust to one's surroundings. A user's somatic response to stimuli may therefore also be used, as in the claimed subject matter, to indicate the user's alignment with his or her conscious self and/or subconscious self.

Figure 1:
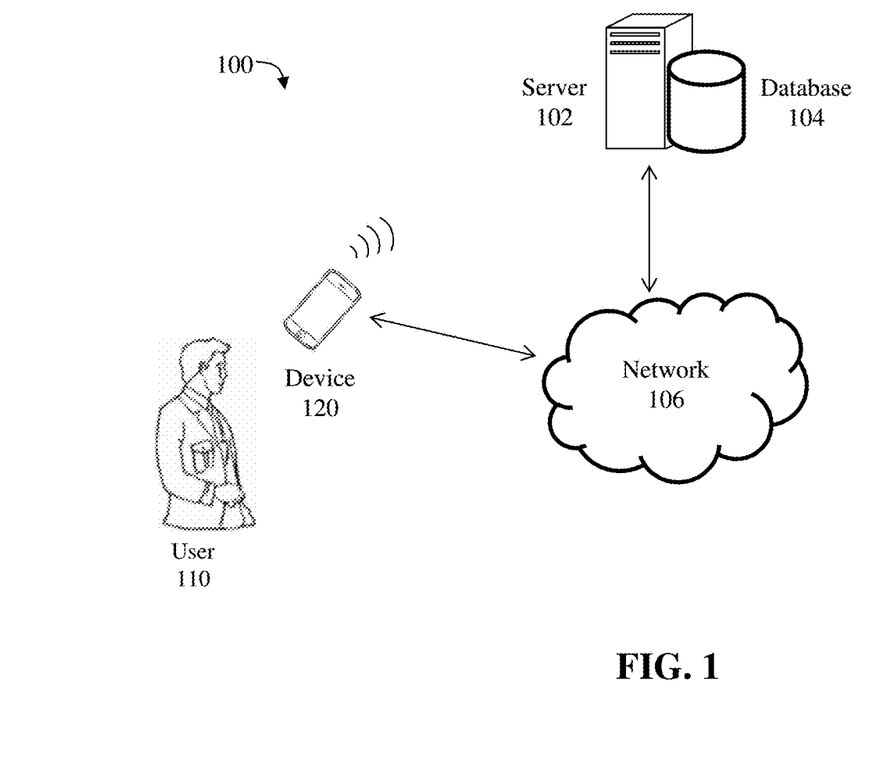
FIG. 1 is a diagram of an operating environment that supports a method and system for measuring somatic response of a user to stimulus, according to an example embodiment.

FIG. 1 is a diagram of an operating environment 100 that supports a method and system for measuring somatic response of a user to stimulus. The server or computing device 102 may be communicatively coupled with a communications network 106, according to an example embodiment. The environment 100 may comprise mobile computing devices 120, which may communicate with computing device (or server) 102 via a communications network 106. Mobile computing device 120 may comprise a cellular/mobile telephone, smart phone, tablet computer, laptop computer, handheld computer, wearable computer, or the like. Device 120 may also comprise other computing devices such as desktop computers, workstations, servers, and game consoles, for example. The mobile computing device 120 may be connected either wirelessly or in a wired or fiber optic form to the communications network 106. Communications network 106 may be a packet switched network, such as the Internet, or any local area network, wide area network, enterprise private network, cellular network, phone network, mobile communications network, or any combination of the above.

The environment 100 shows that mobile computing device 120 is operated by a user 110. Server 102 and device 120 may each comprise a computing device 600, described below in greater detail with respect to FIG. 6. Device 120 may also include one or more motion sensors. Said motion sensors may include an accelerometer, a tilt sensor, a digital compass, a magnetometer, a gyroscope, etc.

Computing device 120 (and/or server 102) may include a software engine that delivers applications, data, program code and other information to networked devices. The software engine of device 120 (or server 102) may perform other processes such as transferring multimedia data in a stream of packets that are interpreted and rendered by a software application as the packets arrive. FIG. 1 further shows that server 102 includes a database or repository 104, which may be a relational database comprising a Structured Query Language (SQL) database stored in a SQL server. Mobile computing device 120 may also include its own database, either locally or via the cloud. The database 104 may serve somatic response data, as well as related information, which may be used by device 102 and mobile computing device 120.

Device 120 and server 102 may each include program logic comprising computer source code, scripting language code or interpreted language code that perform various functions of the disclosed embodiments. In one embodiment, the aforementioned program logic may comprise program module 607 in FIG. 6. It should be noted that although FIG. 1 shows only one mobile computing devices 120 and one server 102, the system of the disclosed embodiments supports any number of servers and mobile computing devices connected via network 106. Also note that although device 120 (and server 102) is shown as a single and independent entity, in one embodiment, device 120 (or server 102) and its functionality can be realized in a centralized fashion in one computer system or in a distributed fashion wherein different elements are spread across several interconnected computer systems.

Database 104 (or a database of device 120) may be used to store supervised data, as well as unsupervised data. Supervised data refers to input data that has a desired output value. In the case of the instant application, supervised data may comprise motion sensor data that is collected from device 120, wherein the type of the supervised is known to be either positive or negative. Positive or negative type of supervised data may refer to the state of mind of the user during the triple whip gesture. Positive type of supervised data may refer to instances when the user is affirming a statement, making a statement of affirmation, making a statement that is true, making a verbal statement of affirmation, making a verbal statement that is true, holding a positive thought in mind, holding a food with which the user has a positive sensitivity, or looking at a food with which the user has a positive sensitivity. Negative type of supervised data may refer to instances where the user is negating a statement, making a statement of negation, making a statement that is false, making a verbal statement of negation, making a verbal statement that is false, holding a negative thought in mind, holding a food with which the user has a negative sensitivity, or looking at a food with which the user has a negative sensitivity. Thus, supervised data may refer to captured motion sensor data wherein the type of the data is known beforehand or is a given.

Unsupervised data refers to input data that has no desired output value. In the case of the instant application, unsupervised data may comprise motion sensor data that is collected from device 120, wherein the type of the supervised is not known to be either positive or negative at the time the data is captured. Thus, unsupervised data may refer to captured motion sensor data wherein the type of the data is calculated by the system at a later time.

In one embodiment, all of the data collected or calculated by device 120 may be transmitted to server 102 via network 106. In another embodiment, data (such as supervised or unsupervised data) may be collected by device 120 and transmitted to server 102 via network 106, wherein server 102 subsequently performs calculations using said data, as described more fully below.

Figure 2:
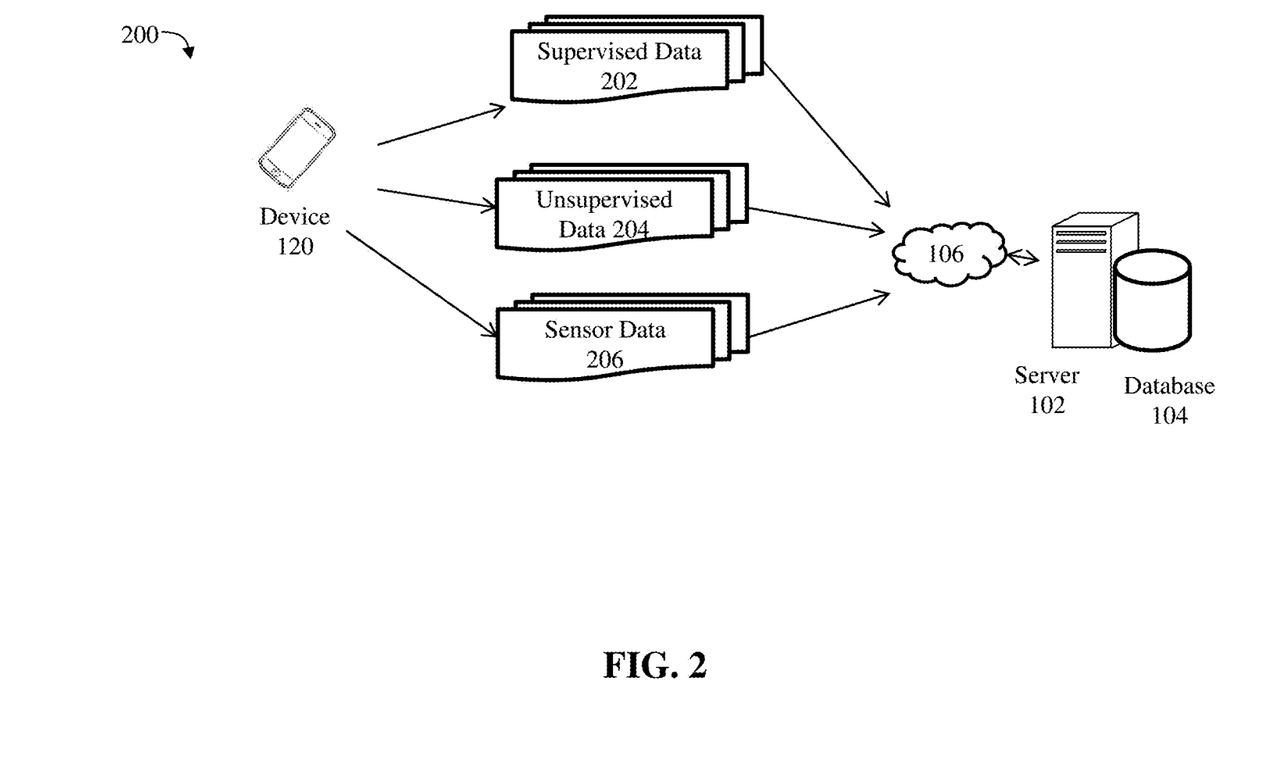
FIG. 2 is a diagram showing the data flow of the general process for measuring somatic response of a user to stimulus, according to an example embodiment.
Figure 3:
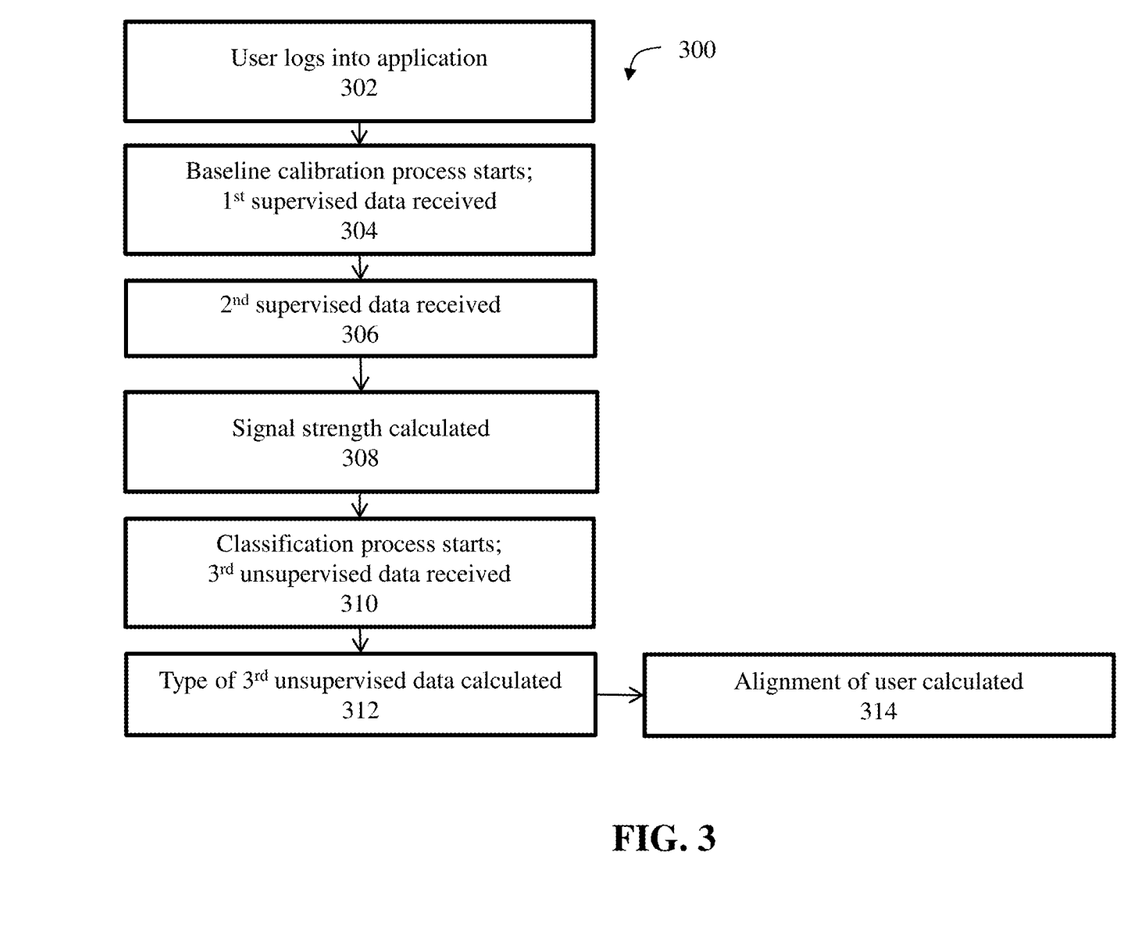
FIG. 3 is a flow chart showing the control flow of the process for measuring somatic response of a user to stimulus, according to an example embodiment.

FIG. 3 is a flow chart showing the control flow of the process for measuring somatic response of a user to stimulus, according to an example embodiment. Process 300 describes the steps that being to occur when the user 110 utilizes device 120 to measure his somatic response to stimulus. The process 300 is described with reference to FIG. 2, which shows the general data flow 200 of the process 300, as well as FIGS. 4 and 5.

Prior to the beginning of the process 300, stored in database 104 (or in a database of device 120) may be a user record that holds data about the user 110, such as name, address, email address, unique identifier, handle, telephone number, age, sex, occupation, marital status, etc. Process 300 starts in earnest with step 302 wherein user 110 logs in to an application, such as a mobile application, on device 120. It should be noted that although the process 300 is described in terms of actions executed by processor 602 on device 120, in one embodiment, any such actions ascribed to processor 602 on device 120 may be performed by a processor on server 102.

Next, processor 602 on device 120 executes a multi-step baseline calibration process. The first step 304 of the baseline calibration process includes receiving a first supervised data 202 comprising a negative type and a first sensor data 206 from the plurality of motion sensors while the user performs a triple whip gesture comprising a wrist movement executed three times while holding the mobile computing device 120. The triple whip gesture is described in more detail below with reference to FIG. 5. The negative type of the supervised data 202 means that during the triple whip gesture, the user is negating a statement, making a statement of negation, making a statement that is false, making a verbal statement of negation, making a verbal statement that is false, holding a negative thought in mind, holding a food with which the user has a negative sensitivity, or looking at a food with which the user has a negative sensitivity.

The step of receiving a first supervised data comprising a negative type may include a preliminary step wherein the device 120 prompts (or provides instructions to) the user, via the interface of device 120, to enter supervised data of a certain type, such as audio, video or a graphic stating that the user must enter supervised data of a certain type. For example, the device 120 may display a statement that reads "please make a negative statement that is false while executing the triple whip gesture", or "please hold a negative thought while executing the triple whip gesture", or "please hold a food with which you have a negative affinity while executing the triple whip gesture" in order to solicit first supervised data comprising a negative type. Alternatively, the user may simply provide input (via an interface in the device 120) that indicates the type of the first supervised data the user will be inputting. The user may provide said input, via the interface of device 120, either before the first supervised data is provided, or afterwards. The step of receiving a first supervised data comprising a negative type may also include a preliminary step wherein the device 120 prompts (or provides instructions to) the user, via the interface of device 120, to perform the triple whip gesture. The device 120 may do so by providing an image or images (or video, as well as audio) similar or identical to the images provides in FIG. 5 below.

Also in step 304, the processor 602 classifies the first sensor data according to a predefined criteria and associates class data with the first sensor data. In step 304, the processor 304 may utilize a predefined criteria to classify the first sensor data. Said classification may comprise considering various aspects, metadata or attributes of the first sensor data, such as the time of completion of the triple whip gesture, the strength of the movement, the speed of the movement, the magnitude of the accelerations involved, the magnitude of the speeds involved, the range of speeds involved, the range of accelerations, and the like. Said classification may involve classifying the first sensor data according to the numerical values of the various aspects of the first sensor data, as described above. Once classified, the processor 602 may then associate class data with the first sensor data. Specifically, attributes or other metadata about said class, in which the first sensor data has been classified, shall be associated with the first sensor data. The purpose of step 304 is to identify the relationship between the negative type and the first sensor data. This relationship can later be used to determine whether certain sensor data should be classified as a positive or a negative type.

Next, in step 306, the processor 602 receives a second supervised data comprising a positive type and a second sensor data from the plurality of motion sensors while the user performs the triple whip gesture. Also in step 306, the processor 602 classifies the second sensor data according to the predefined criteria and associates class data with the second sensor data. Step 306 concludes the multi-step baseline calibration process. The purpose of step 306 is to identify the relationship between the positive type and the second sensor data. This relationship can later be used to determine whether certain sensor data should be classified as a positive or a negative type.

The positive type of the second supervised data means that during the triple whip gesture, the user is affirming a statement, making a statement of affirmation, making a statement that is true, making a verbal statement of affirmation, making a verbal statement that is true, holding a positive thought in mind, holding a food with which the user has a positive sensitivity, or looking at a food with which the user has a positive sensitivity.

The step of receiving a second supervised data comprising a positive type may include a preliminary step wherein the device 120 prompts (or provides instructions to) the user, via the interface of device 120, to enter supervised data of a positive type. For example, the device 120 may display a statement that reads "please make a positive statement that is true while executing the triple whip gesture", or "please hold a positive thought while executing the triple whip gesture", or "please hold a food with which you have a positive affinity while executing the triple whip gesture" in order to solicit second supervised data comprising a positive type. Alternatively, the user may simply provide input (via an interface in the device 120) that indicates the type of the second supervised data the user input.

Then, in step 308, the processor 602 calculates signal strength of the first and second sensor data using a k-means clustering algorithm, wherein the first and second sensor data are clustered based on one or more features of the triple whip gesture embodied in the first and second sensor data, and wherein signal strength comprises a confidence level that unsupervised data may be classified based on the first and second sensor data and class data associated therewith.

k-means clustering is a well-known method of vector quantization that aims to partition multiple observations into k clusters in which each observation belongs to the cluster with the nearest mean. k-means clustering is used to cluster sensor data into one of multiple clusters (such as a positive type cluster and a negative type cluster), according to various aspects, metadata or attributes of the sensor data, such as the time of completion of the triple whip gesture, the strength of the movement, the speed of the movement, the magnitude of the accelerations involved, the magnitude of the speeds involved, the range of speeds involved, the range of accelerations, and the like. In step 308, the first and second sensor data are clustered according to a k-means clustering algorithm.

Also in step 308, the processor 602 calculates signal strength, which comprises a confidence level that unsupervised data may be classified based on the first and second sensor data and class data associated therewith. In this step, the processor 602 evaluates the data clustered using the k-means clustering algorithm and determines how well-defined the clusters appear. If clusters are well-defined, then there are few, if any, outliers, the cluster areas are small, and there is no overlap between the areas defined by clusters. If clusters are not well-defined, then there may be one or more outliers, the cluster areas may be large, and there may be overlap between the areas of clusters. According to how well-defined the areas of the clusters appear, the processor 602 calculates signal strength, which may be displayed by device 120 using a graphic, text, audio or video. Signal strength may be numerical value, such as a continuous range of real number values between 1 and 100 or between 0 and 1.

Then, the processor 602 executes a multi-step classification process. The first step 310 of the multi-step classification calibration process includes reading third unsupervised data 204 comprising third sensor data from the plurality of motion sensors while the user performs the triple whip gesture. Also, in step 310, the processor 602 classifies third sensor data in a cluster defined by the k-means clustering algorithm and associates class data with the third sensor data. Thus, in step 310, the processor 602 attempts to place the third sensor data in one of the clusters defined above by the k-means clustering algorithm. In step 312, the processor 602 determines a type (either negative or positive) of the third sensor data, based on the class data.

Subsequently, in step 314, the user may input whether the third sensor data was either a positive type or negative type. If the type entered by the user in step 314 matches the type calculated by the processor 603 in step 312, then the user is deemed to be aligned or in harmony with his conscious self and/or subconscious self. This scenario illustrates that the user's somatic response (i.e., the whipping gesture) indicates that the type entered by the user does in fact match the type calculated by the system, thereby indicating that the user is aware of, or aligned with, his conscious and/or subconscious self.

If the type entered by the user in step 314 does not match the type calculated by the processor 603 in step 312, then the user is deemed to be misaligned or in dis-harmony with his conscious self. Thus, also in step 314, the processor 602 may display on device 120 a graphical, textual, video and/or audio indicator that indicates whether the user is deemed to be aligned or in harmony with his conscious self and/or subconscious self. This scenario illustrates that the user's somatic response indicates that the type entered by the user does not match the type calculated by the system, thereby indicating that the user is not aware of, or misaligned with, his conscious and/or subconscious self.

Figure 4:
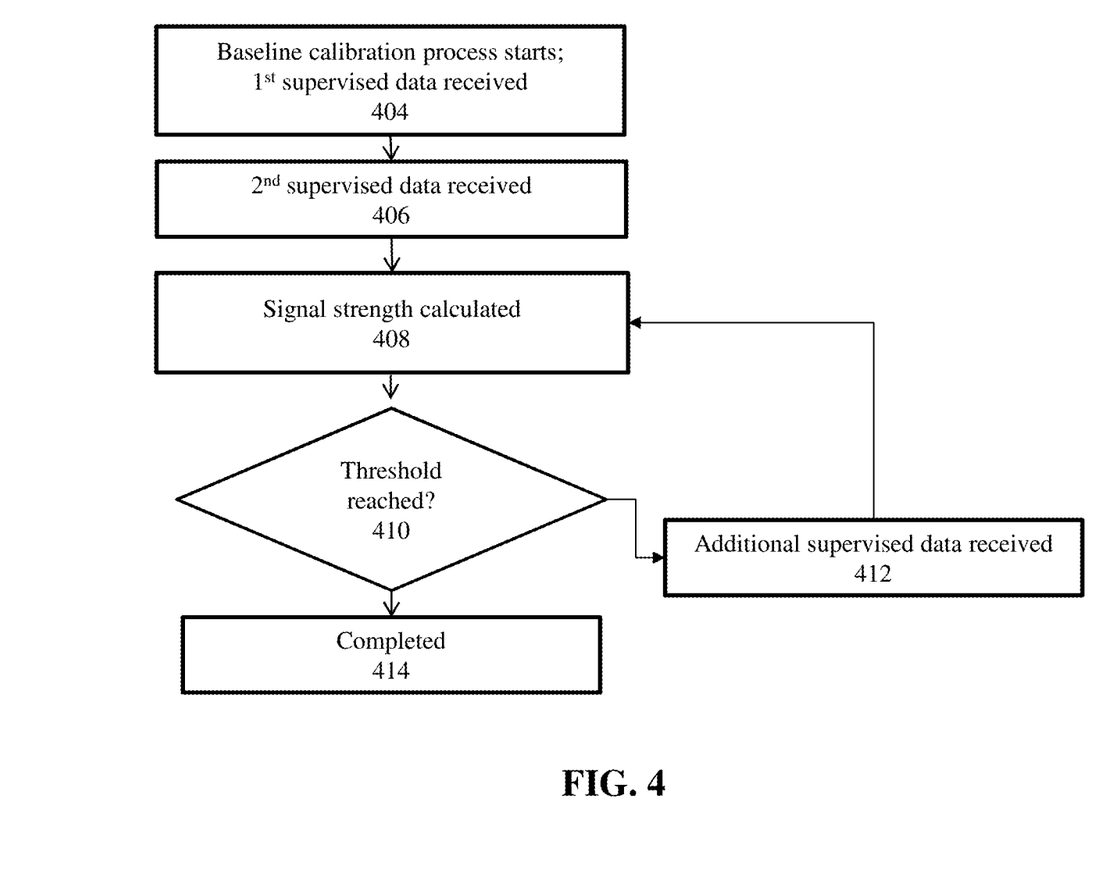
FIG. 4 is a flow chart showing the control flow of an alternative calibration process for measuring somatic response of a user to stimulus, according to an example embodiment.

FIG. 4 is a flow chart showing the control flow of an alternative calibration process for measuring somatic response of a user to stimulus, according to an example embodiment. Steps 404, 406 and 408 are identical to steps 304, 306, and 308 above. But in step 410, the processor 602 inquires whether a predefined threshold signal strength has been reached. If so, then in step 414, the calibration process is completed. If not, in step 412, additional supervised data is collected, and control flows back to step 408 above.

Figure 5:
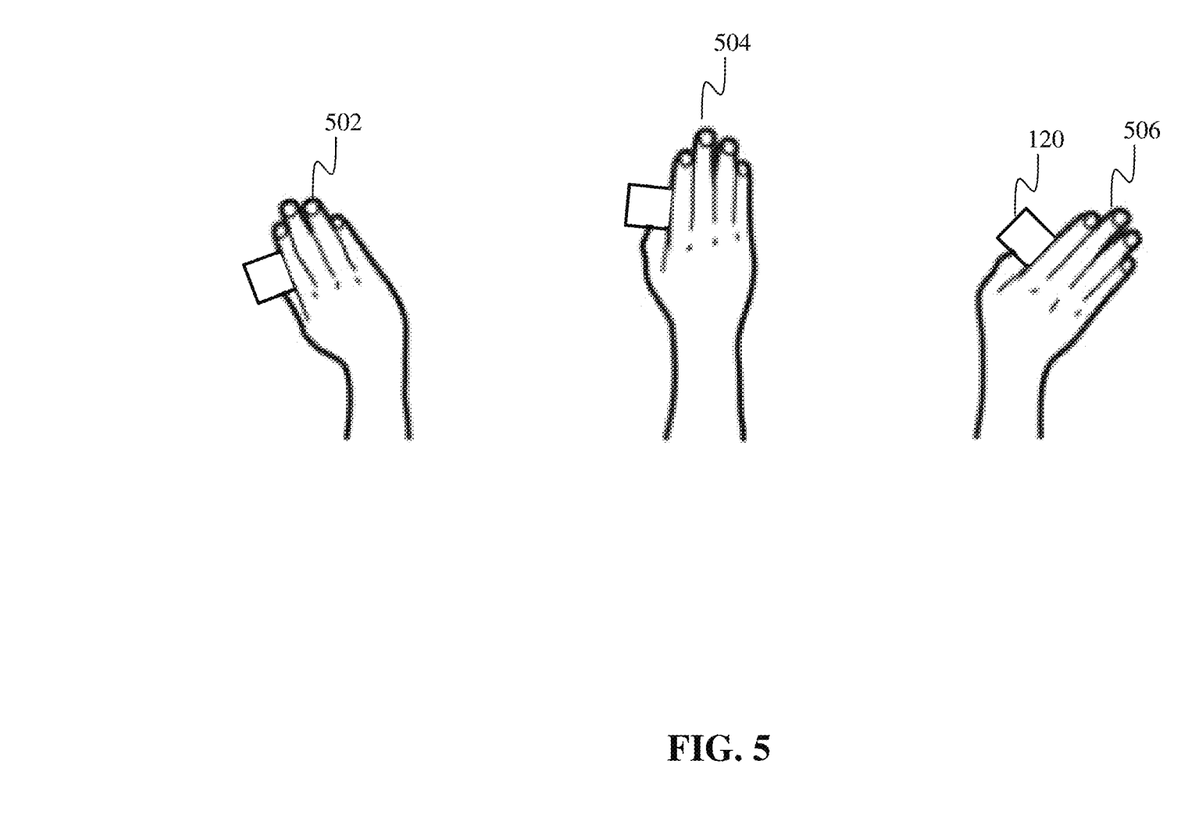
FIG. 5 is an illustration showing a whipping gesture, according to an example embodiment.

FIG. 5 is an illustration showing the hand gesture made by the user, according to an example embodiment. FIG. 5 shows that a whip gesture may comprise holding the device 120 in the user's hand and starting the movement in step 502, wherein the user's hand may move about wrist, such that the hand is deviated toward the left. Next, the user performs a whipping movement that moves the device 120 such that the hand moves about the wrist towards the right, wherein step 504 shows that the user's wrist has moved such that the hand is aligned with the arm and there is no deviation of the hand compared to the arm. Lastly, in step 506, the whipping movement continues to move the device 120 such that the hand moves about the wrist and deviates towards the right. The steps 502-506 show one whipping gesture. A triple whipping gesture may comprise performing this whipping gesture three times.

Figure 6:
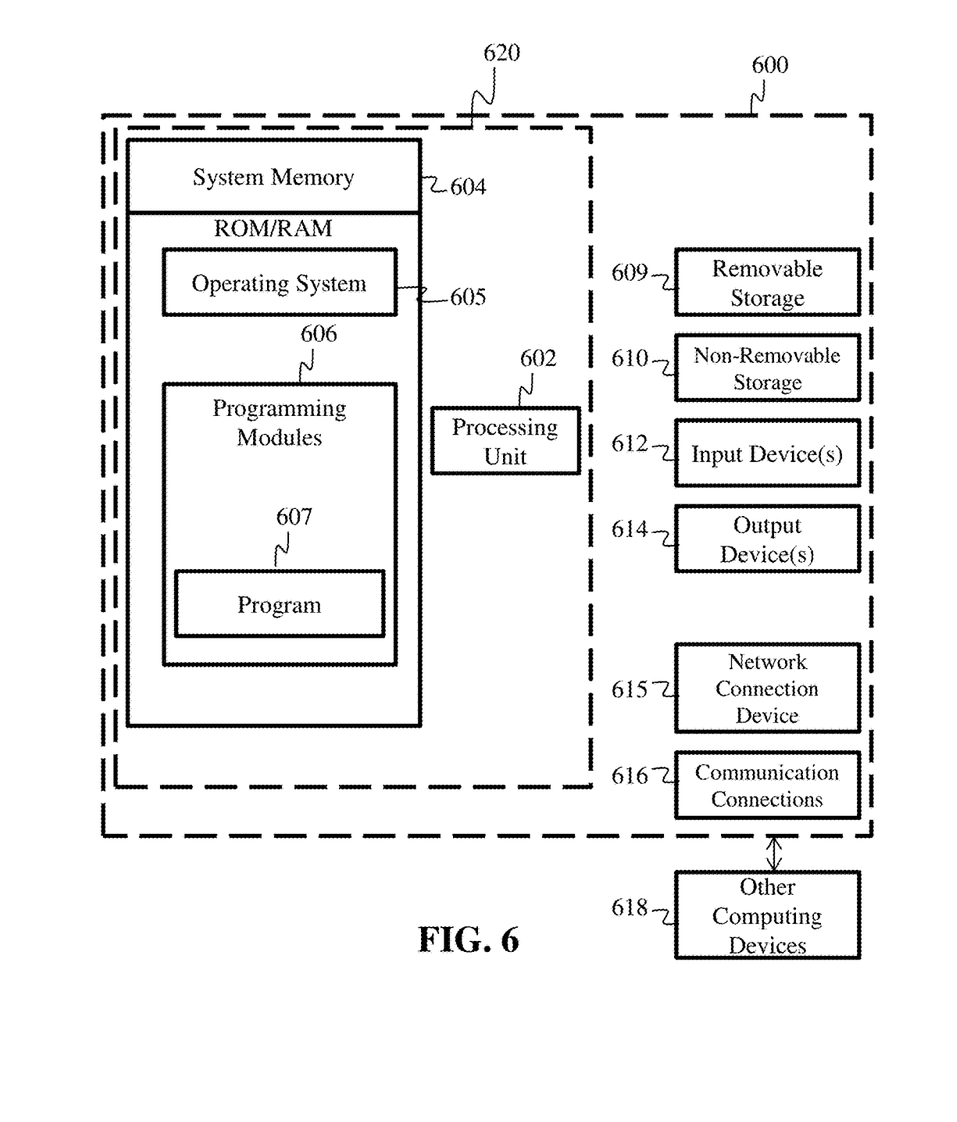
FIG. 6 is a block diagram of a system including a computing device, according to an example embodiment.

FIG. 6 is a block diagram of a system including an example computing device 600 and other computing devices. Consistent with the embodiments described herein, the aforementioned actions performed by device 120 or server 102 may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for system 100 and process 300, as described above. Process 300 may operate in other environments and are not limited to computing device 600.

With reference to FIG. 6, a system consistent with an embodiment of the invention may include a plurality of computing devices, such as computing device 600. In a basic configuration, computing device 600 may include at least one processing unit 602 and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of device 120 or server 102. Furthermore, embodiments of the invention may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of device 600. Computing device 600 may also have input device(s) 612 such as a keyboard, a mouse, a pen, a sound input device, a camera, a touch input device, etc. Output device(s) 614 such as a display, speakers, a printer, etc. may also be included. Computing device 600 may also include a vibration device capable of initiating a vibration in the device on command, such as a mechanical vibrator or a vibrating alert motor. The aforementioned devices are only examples, and other devices may be added or substituted.

Computing device 600 may also contain a network connection device 615 that may allow device 600 to communicate with other computing devices 618, such as over a network in a distributed computing environment, for example, an intranet or the Internet. Device 615 may be a wired or wireless network interface controller, a network interface card, a network interface device, a network adapter or a LAN adapter. Device 615 allows for a communication connection 616 for communicating with other computing devices 618. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g. program module 607) may perform processes including, for example, one or more of the stages of the process 300 as described above. The aforementioned processes are examples, and processing unit 602 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A mobile computing device for measuring somatic response of a user to stimulus, the mobile computing device comprising:

a) a plurality of motion sensors configured for capturing motion sensor data;
b) a volatile memory; and
c) a processor communicatively coupled with the plurality of motion sensors and the memory, the processor configured for:
  1) executing a baseline calibration process comprising: i) receiving a first supervised data comprising a negative type and a first sensor data from the plurality of motion sensors while the user performs a triple whip gesture comprising the user whipping his hand about his wrist while said hand is holding the mobile computing device a total of three times; ii) classifying the first sensor data according to a predefined criteria and associating class data with the first sensor data; iii) receiving a second supervised data comprising a positive type and a second sensor data from the plurality of motion sensors while the user performs the triple whip gesture; iv) classifying the second sensor data according to the predefined criteria and associating class data with the second sensor data;
  2) calculating metadata about the first sensor data, including calculating a time of completion, a strength, one or more speeds, and one or more accelerations pertaining to the triple whip gesture performed by the user when the first supervised data is received;
  3) calculating metadata about the second sensor data, including calculating a time of completion, a strength, one or more speeds, and one or more accelerations pertaining to the triple whip gesture performed by the user when the second supervised data is received;
  4) calculating signal strength of the first and second sensor data using a k-means clustering algorithm, wherein the first and second sensor data are grouped into clusters based on the metadata that was calculated about the first sensor data, and the metadata that was calculated about the second sensor data wherein signal strength is based on both an assessment of how well-defined the clusters are and a numerical confidence level that unsupervised data may be classified into certain clusters based on the first and second sensor data and class data associated therewith; and
  5) executing a classification process comprising: i) reading third unsupervised data comprising third sensor data from the plurality of motion sensors while the user performs the triple whip gesture, ii) classifying the third sensor data in a cluster defined by the k-means clustering algorithm and associating class data with the third sensor data, wherein said class data includes attributes and metadata about a class; and iii) determining a type of the third sensor data, based on the class data.

2. The mobile computing device of claim 1, wherein the processor is further configured for:
  executing a subsequent calibration process comprising: i) receiving a fourth supervised data comprising a given type and a fourth sensor data from the plurality of motion sensors while the user performs a triple whip gesture; ii) classifying the fourth sensor data according to said predefined criteria and associating class data with the fourth sensor data;
  calculating a revised signal strength of all previously read sensor data using the k-means clustering algorithm, wherein all previously read sensor data are clustered based on one or more features of the triple whip gesture embodied in all previously read sensor data.

3. The mobile computing device of claim 1, further comprising:
  a display for displaying user instructions for executing the triple whip gesture.

4. The mobile computing device of claim 3, wherein the display is further configured for prompting the user to hold a negative thought when the user is providing said first supervised data, and for prompting the user to hold a positive thought when the user is providing said second supervised data.

5. The mobile computing device of claim 1, wherein the display is further configured for displaying a graphic representing the signal strength that was calculated.

6. The mobile computing device of claim 1, wherein if the signal strength that was calculated is below a predefined threshold, re-executing the step of executing a baseline calibration process.

7. The mobile computing device of claim 1, wherein the plurality of motion sensors comprises at least one accelerometer.

8. The mobile computing device of claim 7, wherein the plurality of motion sensors comprises at least one accelerometer, at least one gyroscope and at least one magnetometer.

9. The mobile computing device of claim 1, wherein the step of receiving a first supervised data comprising a negative type further comprises receiving the first sensor data from the plurality of motion sensors while the user performs the triple whip gesture, and subsequently receiving from the user, via an interface of the mobile computing device, an indicator that the first supervised data is the negative type; and
  wherein the step of receiving a second supervised data comprising a positive type further comprises receiving the second sensor data from the plurality of motion sensors while the user performs the triple whip gesture, and subsequently receiving from the user, via the interface of the mobile computing device, an indicator that the second supervised data is the positive type.

10. The mobile computing device of claim 1, wherein the step of receiving a first supervised data comprising a negative type further comprises receiving the first sensor data from the plurality of motion sensors while the user performs the triple whip gesture while holding a food with which the user has a negative sensitivity, and subsequently receiving from the user, via an interface of the mobile computing device, an indicator that the first supervised data is the negative type; and
  wherein the step of receiving a second supervised data comprising a positive type further comprises receiving the second sensor data from the plurality of motion sensors while the user performs the triple whip gesture while holding a food with which the user has a positive sensitivity, and subsequently receiving from the user, via the interface of the mobile computing device, an indicator that the second supervised data is the positive type.

11. The mobile computing device of claim 10, wherein the display is further configured for prompting the user to make a verbal statement of negation when the user is providing said first unsupervised data.

12. The mobile computing device of claim 11, wherein the display is further configured for prompting the user to make a verbal statement of affirmation when the user is providing said second unsupervised data.

13. The mobile computing device of claim 12, wherein the display is further configured for
displaying a graphic representing the type of the third sensor data.

14. The mobile computing device of claim 2, wherein the step of receiving a third unsupervised data further comprises receiving the third sensor data from the plurality of motion sensors while the user performs the triple whip gesture while holding a food with which the user has a negative sensitivity, and subsequently receiving from the user, via an interface of the mobile computing device, an indicator that the third unsupervised data is the negative type; and
wherein the step of receiving a fourth unsupervised data further comprises receiving the fourth sensor data from the plurality of motion sensors while the user performs the triple whip gesture while holding a food with which the user has a positive sensitivity, and subsequently receiving from the user, via the interface of the mobile computing device, an indicator that the fourth unsupervised data is the positive type.

15. A mobile computing device for measuring somatic response of a user to stimulus, the mobile computing device comprising:
a) a plurality of motion sensors configured for capturing motion sensor data;
b) a display for displaying user instructions for executing a triple whip gesture comprising an arm movement executed three times while holding the mobile computing device;
c) a volatile memory; and
d) a processor communicatively coupled with the plurality of motion sensors and the memory, the processor configured for:
1) executing a baseline calibration process comprising: i) receiving a first supervised data comprising a negative type and a first sensor data from the plurality of motion sensors while the user performs a triple whip gesture comprising the user whipping his hand about his wrist while said hand is holding the mobile computing device a total of three times; ii) classifying the first sensor data according to a predefined criteria and associating class data with the first sensor data; iii) receiving a second supervised data comprising a positive type and a second sensor data from the plurality of motion sensors while the user performs the triple whip gesture; iv) classifying the second sensor data according to the predefined criteria and associating class data with the second sensor data;
2) calculating metadata about the first sensor data, including calculating a time of completion, a strength, one or more speeds, and one or more accelerations pertaining to the triple whip gesture performed by the user when the first supervised data is received;
3) calculating metadata about the second sensor data, including calculating a time of completion, a strength, one or more speeds, and one or more accelerations pertaining to the triple whip gesture performed by the user when the second supervised data is received;
4) calculating signal strength of the first and second sensor data using a k-means clustering algorithm, wherein the first and second sensor data are grouped into clusters based on the metadata that was calculated about the first sensor data, and the metadata that was calculated about the second sensor data wherein signal strength is based on both an assessment of how well-defined the clusters are and a numerical confidence level that unsupervised data may be classified into certain clusters based on the first and second sensor data and class data associated therewith; and
5) executing a classification process comprising: i) reading third unsupervised data comprising third sensor data from the plurality of motion sensors while the user performs the triple whip gesture, ii) classifying the third sensor data in a cluster defined by the k-means clustering algorithm and associating class data with the third sensor data wherein said class data includes attributes and metadata about a class; and iii) determining a type of the third sensor data, based on the class data.

16. The mobile computing device of claim 15, wherein the processor is further configured for:
executing a subsequent calibration process comprising: i) receiving a fourth supervised data comprising a given type and a fourth sensor data from the plurality of motion sensors while the user performs a triple whip gesture; ii) classifying the fourth sensor data according to said predefined criteria and associating class data with the fourth sensor data;
calculating a revised signal strength of all previously read sensor data using the k-means clustering algorithm, wherein all previously read sensor data are clustered based on one or more features of the triple whip gesture embodied in all previously read sensor data.

17. The mobile computing device of claim 16, wherein the display is further configured for prompting the user to hold a negative thought when the user is providing said first supervised data, and for prompting the user to hold a positive thought when the user is providing said second supervised data.

18. The mobile computing device of claim 15, further comprising:
receiving from the user, via the interface of the mobile computing device, an indicator of the type of the third unsupervised data;
if the indicator of the type entered by the user matches the type of the third sensor data determined by the mobile computing device, then displaying a graphic indicating that the third sensor data matches the indicator of the type entered by the user, thereby suggesting that the user's somatic response is aligned with his conscious self; and
if the indicator of the type entered by the user does not match the type of the third sensor data determined by the mobile computing device, then displaying a graphic indicating that the third sensor data differed from the indicator of the type entered by the user and therefore the user's somatic response is not aligned with his conscious self.

* * * * *